United States Patent
Chih et al.

(10) Patent No.: US 10,806,666 B2
(45) Date of Patent: Oct. 20, 2020

(54) NEEDLE-FREE CONNECTION DEVICE

(71) Applicant: Lily Medical Corporation, Miaoli County (TW)

(72) Inventors: Yung-Hung Chih, Miaoli County (TW); Chih-Jung Chen, Miaoli County (TW); Hsien-Chih Tsai, Miaoli County (TW); Yu-Hung Chu, Miaoli County (TW)

(73) Assignee: Lily Medical Corporation, Miaoli County (TW)

( * ) Notice: Subject to any disclaimer, the term of this patent is extended or adjusted under 35 U.S.C. 154(b) by 366 days.

(21) Appl. No.: 15/917,858

(22) Filed: Mar. 12, 2018

(65) Prior Publication Data

US 2018/0296439 A1 Oct. 18, 2018

(30) Foreign Application Priority Data

Apr. 14, 2017 (CN) .......................... 2017 1 0244903

(51) Int. Cl.
*A61J 1/20* (2006.01)
*A61M 39/26* (2006.01)

(52) U.S. Cl.
CPC ........... *A61J 1/2058* (2015.05); *A61J 1/2096* (2013.01); *A61M 39/26* (2013.01); *A61M 2039/263* (2013.01); *A61M 2039/267* (2013.01)

(58) Field of Classification Search
CPC .................. A61J 1/2058; A61J 1/2096; A61M 2039/263; A61M 2039/267; A61M 39/26
See application file for complete search history.

(56) References Cited

U.S. PATENT DOCUMENTS

2002/0133124 A1*  9/2002  Leinsing .............. A61M 39/26
                                                     604/256

FOREIGN PATENT DOCUMENTS

| CN | 1774278 A | 5/2006 | |
|---|---|---|---|
| CN | 1802183 A | 7/2006 | |
| TW | 201438780 | * 10/2014 | ............. A61M 5/32 |
| TW | 201438780 A | 10/2014 | |
| TW | I537020 B | 10/2014 | |

OTHER PUBLICATIONS

Office action of counterpart application by Taiwan IP Office dated May 9, 2018.
Office action of counterpart application by SIPO dated May 11, 2020.

* cited by examiner

*Primary Examiner* — Kai H Weng

(57) ABSTRACT

A needle-free connection device include a casing, a connection base, a slide element and a resilient valve. The casing includes a first hollow tube having a first liquid transmission channel. The connection base is connected to the casing. The resilient valve includes a second hollow tube and a plug connected thereto, wherein the second hollow tube has a second liquid transmission channel, a third liquid transmission channel is formed between the second hollow tube and the plug, and a fourth liquid transmission channel is formed between the connection base and the plug. The first to the fourth liquid transmission channel are intercommunicated with each other. The connection base includes a third hollow tube, and a fourth liquid transmission channel is formed between the plug and the third hollow tube. The needle-free connection device provides a liquid transmission path sequentially passing through the first to the fourth liquid transmission channel.

9 Claims, 4 Drawing Sheets

NEEDLE-FREE CONNECTION DEVICE

This application claims the benefit of People's Republic of China application Serial No. 201710244903.8, filed on Apr. 14, 2017, the subject matter of which is incorporated herein by reference.

BACKGROUND OF THE INVENTION

Field of the Invention

The invention relates in general to a needle-free connection device, and more particularly to a needle-free connection device having multiple liquid transmission channels.

Description of the Related Art

The liquid medicine syringe is used for injecting a liquid medicine into the patient's body. The conventional liquid medicine syringe has a needle disposed on the syringe, and the liquid medicine inside the medicine bottle is injected to the liquid medicine syringe through the needle. However, the needle may easily ruptures stuffs or may hurt the medical staff. In response to the needs, a needle-free liquid medicine syringe without using any needles is provided.

During the use of the needle-free liquid medicine syringe, a liquid transmission channel is formed between the interior of the needle-free connection device and the interior of the reagent feeder when the needle-free connection device and the reagent feeder are coupled together. Then, the liquid medicine inside the medicine bottle can be injected to the liquid medicine syringe through the liquid transmission channel.

However, the air-tight effect of the needle-free connection device of the current technology is unsatisfactory. Quite often, the liquid medicine may easily leak when the user tries to detach the reagent feeder from the needle-free connection device on the completion of injection. Moreover, too many residuals of liquid medicine in the needle-free connection device is an unnecessary waste.

Therefore, how to provide a new needle-free connection device capable of avoiding leakage of liquid medicine and at the same time reducing the residuals of liquid medicine has become a prominent task for the industries. In a generally known design, such as "A needle-free connection device capable of avoiding leakage of liquid medicine" as disclosed in Taiwanese Patent Application No. 102112442, leakage of liquid medicine is avoided through the design of a sleeve and a resilient valve tightly sealed together.

SUMMARY OF THE INVENTION

The invention is directed to a needle-free connection device including a casing, a connection base, a resilient valve and a slide element. The casing includes a first hollow tube having a first liquid transmission channel. The connection base is connected to the casing. The resilient valve includes a second hollow tube and a plug connected with each other, wherein the second hollow tube has a second liquid transmission channel, a third liquid transmission channel is formed between the second hollow tube and the plug, and a fourth liquid transmission channel is formed between the connection base and the plug. The first liquid transmission channel, the second liquid transmission channel, the third liquid transmission channel and the fourth liquid transmission channel are intercommunicated with each other. One end of the slide element leans on the resilient valve. The connection base includes a third hollow tube in which the plug is disposed. The fourth liquid transmission channel is formed between an outer sidewall of the plug and an inner sidewall of the third hollow tube. The needle-free connection device provides a liquid transmission path sequentially passing through the first liquid transmission channel, the second liquid transmission channel, the third liquid transmission channel and the fourth liquid transmission channel. When the slide element is not pushed, the resilient valve returns to original state, such that the liquid transmission path is unable to communicate with the exterior.

The above and other aspects of the invention will become better understood with regard to the following detailed description of the preferred but non-limiting embodiment(s). The following description is made with reference to the accompanying drawings.

DETAILED DESCRIPTION OF THE INVENTION

Figure 1A:
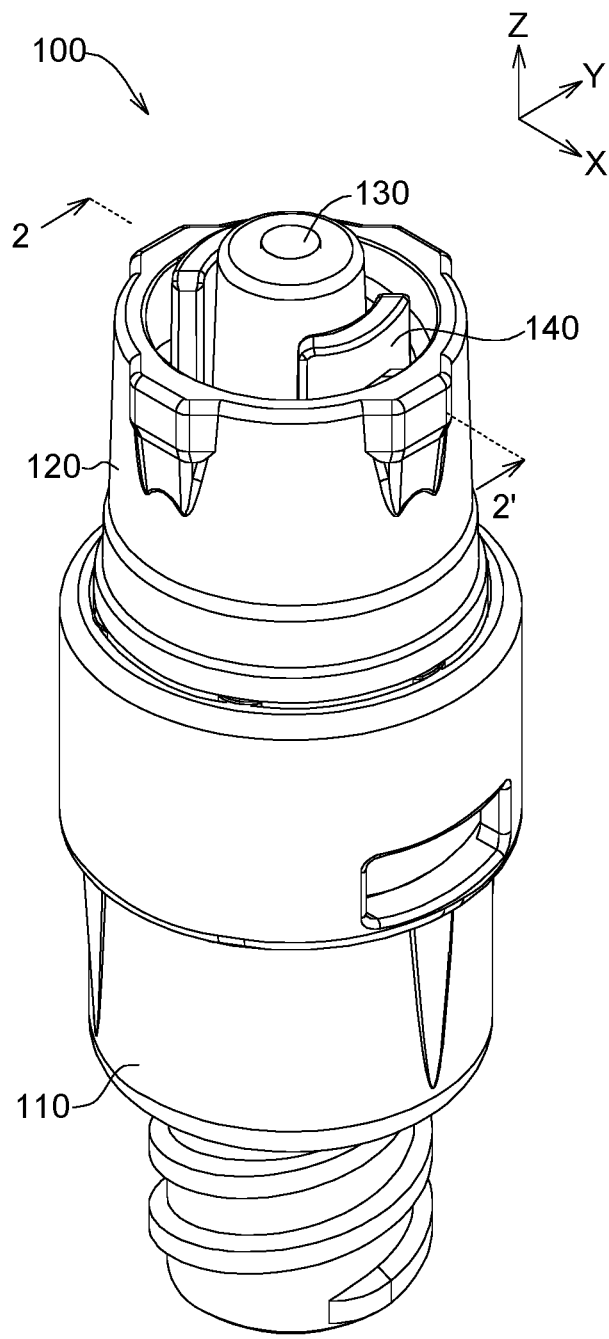
FIG. 1A is an external view of a needle-free connection device according to an embodiment of the invention.
Figure 1B:
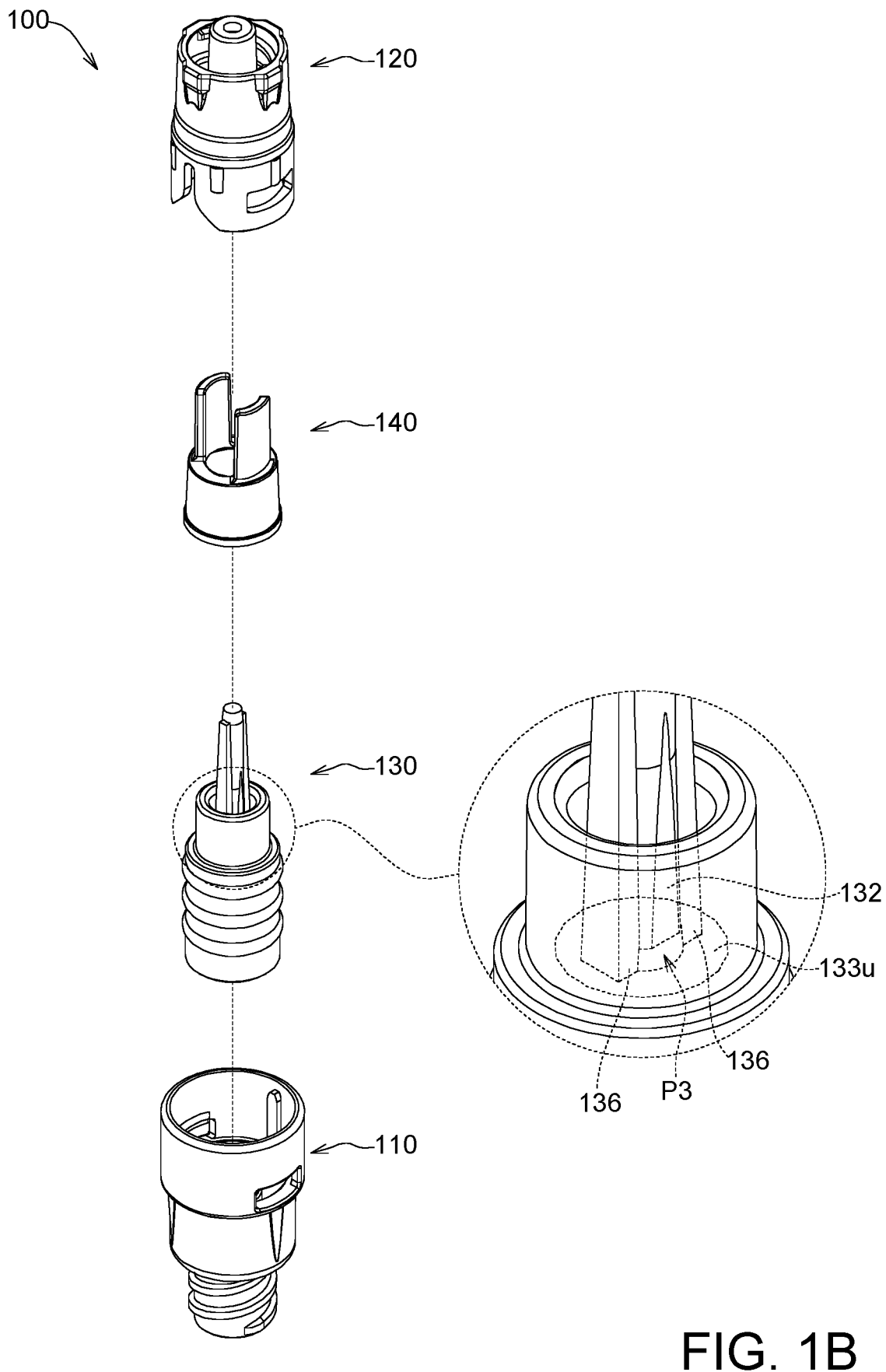
FIG. 1B is an explosion diagram of the needle-free connection device of FIG. 1A.
Figure 2:
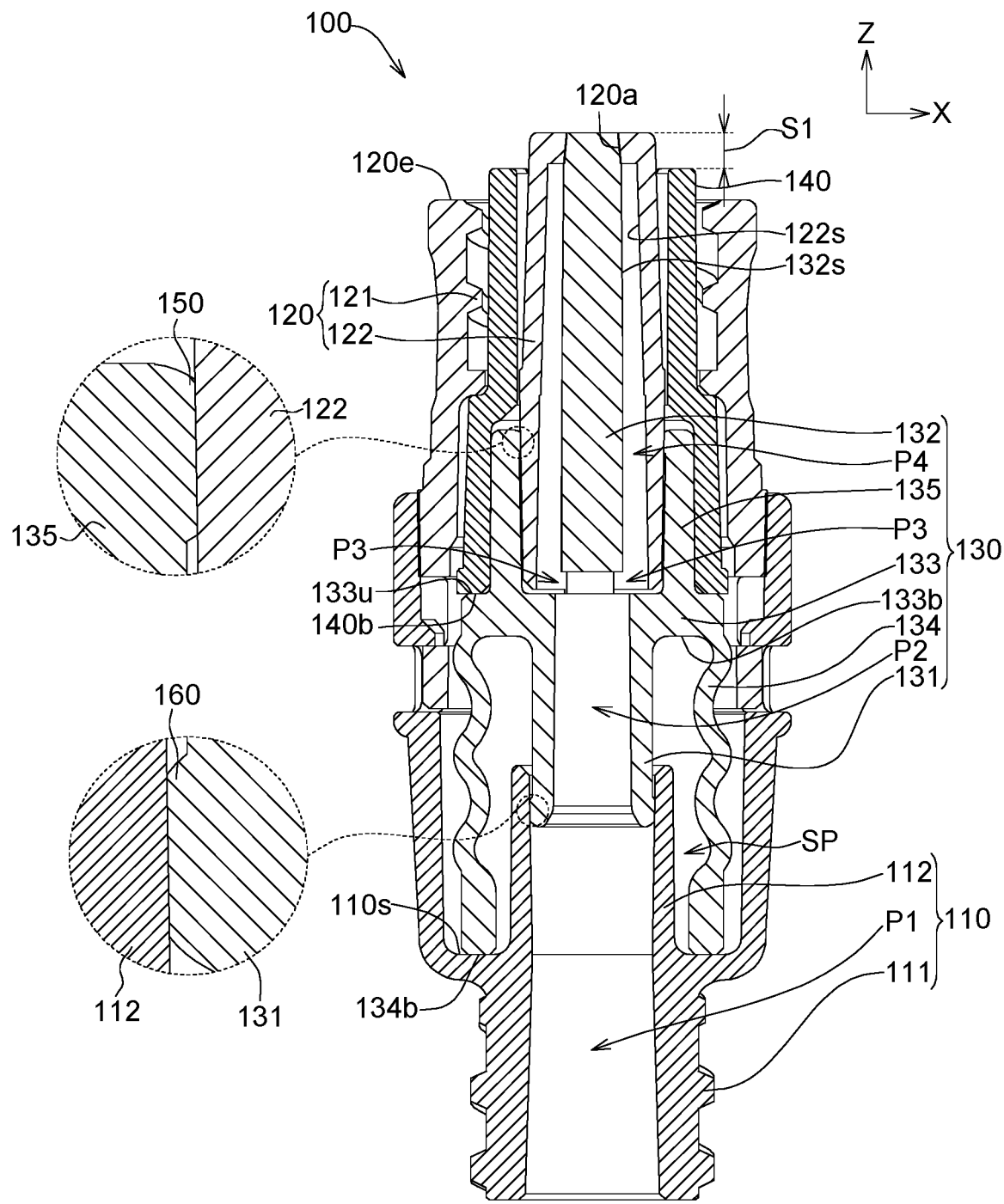
FIG. 2 is a cross-sectional view of the needle-free connection device of FIG. 1A along a direction 2-2'.
Figure 3:
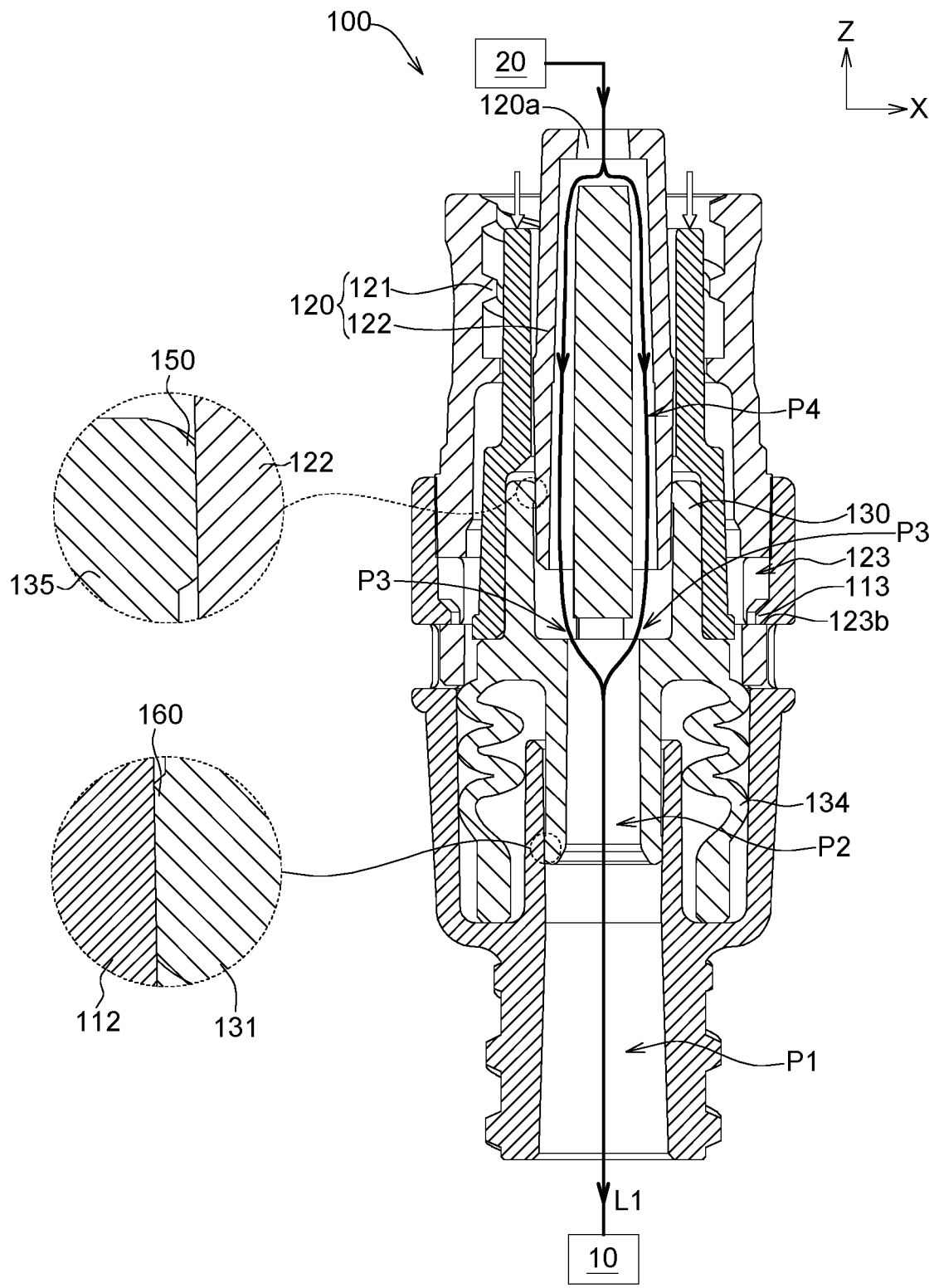
FIG. 3 is a schematic diagram of the needle-free connection device of FIG. 2 connected to a reagent feeder.

Refer to FIGS. 1A, 1B, 2 and 3. FIG. 1A is an external view of a needle-free connection device 100 according to an embodiment of the invention. FIG. 1B is an explosion diagram of the needle-free connection device 100 of FIG. 1A. FIG. 2 is a cross-sectional view of the needle-free connection device 100 of FIG. 1A along a direction 2-2'. FIG. 3 is a schematic diagram of the needle-free connection device 100 of FIG. 2 connected to a reagent feeder 20.

As indicated in FIGS. 1B and 2, the needle-free connection device 100 is a needle-free connection device capable of preventing leakage of liquid medicine L1 (illustrated in FIG. 3). The needle-free connection device 100 includes a casing 110, a connection base 120, a resilient valve 130 and a slide element 140. An outer sidewall of the casing 110 has an outer thread 111 which can be engaged with a syringe 10 (the syringe 10 is illustrated in FIG. 3). An inner sidewall of the connection base 120 has an inner thread 121 which can be engaged with one end of a reagent feeder 20. The other end of the reagent feeder 20 is coupled with a medicine bottle. During the screw-in process of engaging the reagent feeder 20 with the inner thread 121 of the connection base 120, the reagent feeder 20 pushes the slide element 140 to the interior of the connection base 120. As indicated in FIG. 3, when the resilient valve 130 is squeezed by the slide element 140, the resilient valve 130 becomes deformed and exposes an opening 120a of the connection base 120, such that the liquid medicine L1 inside the medicine bottle can be transmitted to the syringe 10 through the reagent feeder 20 and the opening 120a.

As indicated in FIG. 2, the casing 110 includes a first hollow tube 112 having a first liquid transmission channel P1. The resilient valve 130 includes a second hollow tube 131 and a plug 132 connected with each other, wherein the second hollow tube 131 has a second liquid transmission channel P2, at least one third liquid transmission channel P3 is formed between the second hollow tube 131 and the plug 132, and a fourth liquid transmission channel P4 is formed between the connection base 120 and the plug 132. The connection base 120 is connected to the casing 110 and includes a third hollow tube 122 in which the plug 132 is disposed. The fourth liquid transmission channel P4 is formed between an outer sidewall 132s of the plug 132 and an inner sidewall 122s of the third hollow tube 122.

The first liquid transmission channel P1, the second liquid transmission channel P2, the third liquid transmission channel P3 and the fourth liquid transmission channel P4 form a liquid transmission path of the liquid medicine L1. As indicated in FIG. 3, during the process of pushing the resilient valve 130 to the interior of the needle-free connection device 100, the syringe 10 sequentially passes through the first liquid transmission channel P1, the second liquid transmission channel P2, the third liquid transmission channel P3 and the fourth liquid transmission channel P4. Then, the syringe 10 is connected to the reagent feeder 20 for absorbing the liquid medicine inside the medicine bottle through the opening 120a of the connection base 120. Besides, after absorbing the liquid medicine, the syringe 10 sequentially passes through the first liquid transmission channel P1, the second liquid transmission channel P2, the third liquid transmission channel P3 and the fourth liquid transmission channel P4 and then injects the liquid medicine through an opening 120a of the connection base 120.

As indicated in FIG. 2, the resilient valve 130 further includes a receiving portion 133, wherein the second hollow tube 131 extends from a lower surface 133b of the receiving portion 133. As indicated in the enlarged views of FIG. 1B, the needle-free connection device 100 further includes multiple connection portions 136 which are separated from each other and connect the plug 132 with the upper surface 133u of the receiving portion 133. Multiple third liquid transmission channels P3 (only one is illustrated in FIG. 2) separated from each other are formed between the connection portions 136 to provide a diversion function. As indicated in FIG. 3, after the liquid medicine L1 of the syringe 10 flows through the first liquid transmission channel P1 and the second liquid transmission channel P2 in one stream, the liquid medicine L1 is then diverted into multiple streams in the multiple third liquid transmission channels P3. After the liquid medicine L1 flows through the multiple third liquid transmission channels P3 in multiple streams, the multiple streams of liquid medicine L1 are merged into one single stream which accordingly enters the fourth liquid transmission channel P4. The fourth liquid transmission channel P4 surrounds the outer sidewall 132s of the plug 132 along a closed ring. That is, the fourth liquid transmission channel P4 forms a closed ring when viewed from a top view direction of FIG. 2. Thus, the multiple streams of liquid medicine L1 flowing through the multiple third liquid transmission channels P3 are merged into one single annular stream of liquid medicine L1 in the fourth liquid transmission channel P4.

As indicated in FIG. 2, the slide element 140 can be protruded from a terminal surface 120e of the connection base 120. However, the length S1 by which the slide element 140 is protruded from the terminal surface 120e depends on the displacement course of the plug 132 of the resilient valve 130, and the embodiment of the invention is not limited thereto.

As indicated in FIG. 3, the casing 110 and the connection base 120 can be coupled together by way of engaging. For example, the casing 110 includes at least one engaging flange 113 disposed on an inner sidewall of the casing 110, the connection base 120 has at least one first engaging hole 123, and the engaging flange 113 presses a bottom surface 123b of the first engaging hole 123. Thus, the amount of displacement of the casing 110 and the connection base 120 along the Z axis can be limited, and the casing 110 and the connection base 120 can be engaged together and will not be separated easily. In comparison to the ultra-sound coupling, the coupling of the casing 110 and the connection base 120 requires shorter time and incurs lower cost. Moreover, in comparison to the ultra-sound coupling, the coupling of the casing 110 and the connection base 120 is temporary, and the casing 110 and the connection base 120 can be selectively coupled together or separated from each other.

As indicated in FIG. 2, the resilient valve 130 further includes a deformable portion 134 extending to an inner surface 110s of the casing 110 from a lower surface 133b of the receiving portion 133. Furthermore, one end of the slide element 140 leans on the resilient valve 130. For example, a lower surface 140b of one end of the slide element 140 and an upper surface 133u of the receiving portion 133 of the resilient valve 130 are disposed oppositely, such that when the slide element 140 is pushed downwards, as indicated in FIG. 3, the lower surface 140b of the slide element 140 can lean on the upper surface 133u of the receiving portion 133 and push the resilient valve 130 to move downwards. During the downward displacement of the resilient valve 130, the plug 132 of the resilient valve 130 also moves downwards and exposes the opening 120a as indicated in FIG. 3. As indicated in FIG. 2, the deformable portion 134 extends to the inner surface 110s of the casing 110. During the downward displacement of the resilient valve 130, the bottom end 134b of the deformable portion 134 is stopped by the inner surface 110s, such that the deformable portion 134 becomes deformed as indicated in FIG. 3. In comparison to the deformation caused by extension, the deformation of the deformable portion 134 is caused by compression, therefore the deformable portion 134 has a longer fatigue lifespan.

Moreover, the resilient valve 130 has elasticity. During the upward displacement of the slide element 140, the resilient valve 130 is released and returns to a free state as indicated in FIG. 2. After the resilient valve 130 returns to the free state, the plug 132 stuffs the opening 120a to avoid the liquid medicine L1 being leaked from the fourth liquid transmission channel P4. In other words, when the slide element 140 is not pushed, the resilient valve 130 returns its original state, such that the liquid transmission path is unable to communicate with the exterior.

As indicated in FIG. 2, the resilient valve 130 further includes a fourth hollow tube 135. The deformable portion 134 and the fourth hollow tube 135 respectively extends from the lower surface 133b and the upper surface 133u of the receiving portion 133. The deformable portion 134 can have a wavy structure for providing a better flexibility. However, the geometric structure of the deformable portion 134 is not limited in the embodiment of the invention, and any geometric structure would do as long as the deformable portion 134 can provide flexibility. As indicated in FIG. 2, the fourth hollow tube 135 can extend linearly and does not have bending structure, wavy structure and/or corrugated structure. As indicated in FIG. 2, only one of the two structures extending from two opposite sides of the receiving portion 133 of the resilient valve 130 (such as the deformable portion 134 and the fourth hollow tube 135) has a wavy structure or a bending structure, but the embodiment of the invention is not limited thereto.

As indicated in FIG. 2, the second hollow tube 131, the plug 132, the receiving portion 133, the deformable portion 134 and the fourth hollow tube 135 of the resilient valve 130 can be integrally formed in one piece. In terms of the manufacturing process, the second hollow tube 131, the plug 132, the receiving portion 133, the deformable portion 134 and the fourth hollow tube 135 can be integrally formed in one piece in the same manufacturing process. In terms of the materials, the second hollow tube 131, the plug 132, the receiving portion 133, the deformable portion 134 and the fourth hollow tube 135 can be formed of rubber, plastics or other suitable materials.

As indicated in FIG. 2, the deformable portion 134 of the resilient valve 130 is connected to the second hollow tube 131 through the receiving portion 133, and an isolation space SP is formed between the deformable portion 134 and the second hollow tube 131. The isolation space SP separates the first liquid transmission channel P1 from the second liquid transmission channel P2, such that the liquid medicine L1 inside the first liquid transmission channel P1 and the second liquid transmission channel P2 will not be leaked to the isolation space SP. Thus, the problem of the liquid medicine L1 being trapped in the indent of the deformable portion 134 and unable to be transmitted to the reagent feeder 20 can be improved or avoided, the liquid medicine L1 will not be wasted and/or leaked, and the proportion of medicine will not be affected.

As indicated in the enlarged views of FIG. 2, the fourth hollow tube 135 of the resilient valve 130 is disposed between the third hollow tube 122 of the connection base 120 and the slide element 140. The needle-free connection device 100 further includes a first sealing ring 150 being compressed between the third hollow tube 122 and the fourth hollow tube 135 to avoid the liquid medicine L1 being leaked from the channels. The first sealing ring 150 can be a closed ring for providing a circumferential sealing effect. Furthermore, the liquid medicine L1 inside the needle-free connection device 100 presses the inner sidewall 122s of the third hollow tube 122 to squeeze the first sealing ring 150, such that the amount of compression of the first sealing ring 150 can be increased and the third hollow tube 122 and the fourth hollow tube 135 can be sealed more tightly.

In the present embodiment, the first sealing ring 150 can be fixedly disposed on the fourth hollow tube 135 and linked to the fourth hollow tube 135. As indicated in the enlarged view of FIG. 3, when the fourth hollow tube 135 is displaced downwards, the first sealing ring 150 is also displaced downwards, such that the sealing effect of the resilient valve 130 can be maintained during the displacement process. In other words, during the displacement process of the fourth hollow tube 135, the first sealing ring 150 is always between the third hollow tube 122 and the fourth hollow tube 135, such that the sealing effect can be maintained. In an embodiment, the first sealing ring 150 and the fourth hollow tube 135 can be integrally formed in one piece. In terms of the manufacturing process, the first sealing ring 150 and the fourth hollow tube 135 can be integrally formed in one piece in the same manufacturing process. In terms of the materials, the first sealing ring 150 can be formed of rubber, plastics or other suitable materials.

As indicated in the enlarged views of FIG. 2, the needle-free connection device 100 further includes a second sealing ring 160 being compressed between the first hollow tube 112 and the second hollow tube 131 to avoid the liquid medicine L1 being leaked from the channels. During the displacement process of the second hollow tube 131, the second sealing ring 160 is always between the first hollow tube 112 and the second hollow tube 131 such that the sealing effect can be maintained. The second sealing ring 160 can be a closed ring for providing a circumferential sealing effect. Moreover, the liquid medicine L1 inside the needle-free connection device 100 presses an inner sidewall of the second hollow tube 131 to squeeze the second sealing ring 160, such that the amount of compression of the second sealing ring 160 can be increased and the first hollow tube 112 and the second hollow tube 131 can be sealed more tightly.

The second sealing ring 160 can be fixedly disposed on the second hollow tube 131. In the present embodiment, the second sealing ring 160 and the second hollow tube 131 can be integrally formed in one piece. In terms of the manufacturing process, the second sealing ring 160 and the second hollow tube 131 can be integrally formed in one piece in the same manufacturing process. In terms of the materials, the second sealing ring 160 can be formed of rubber, plastics or other suitable materials.

While the invention has been described by way of example and in terms of the preferred embodiment(s), it is to be understood that the invention is not limited thereto. On the contrary, it is intended to cover various modification and similar arrangements and procedures, and the scope of the appended claims therefore should be accorded the broadest interpretation so as to encompass all such modification and similar arrangements and procedures.

What is claimed is:

1. A needle-free connection device, comprising:
    a casing comprising a first hollow tube having a first liquid transmission channel;
    a connection base connected to the casing;
    a resilient valve comprising a second hollow tube and a plug connected with each other, wherein the second hollow tube has a second liquid transmission channel, a third liquid transmission channel is formed between the second hollow tube and the plug, and a fourth liquid transmission channel is formed between the connection base and the plug;
    a slide element whose one end leans on the resilient valve, wherein the first liquid transmission channel, the second liquid transmission channel, the third liquid transmission channel and the fourth liquid transmission channel are intercommunicated with each other;
    wherein the connection base comprises a third hollow tube in which the plug is disposed, and the fourth liquid transmission channel is formed between an outer sidewall of the plug and an inner sidewall of the third hollow tube; and
    wherein when the slide element is pushed to drive the resilient valve, the whole of the resilient valve is movable with respect to the casing, and the needle-free connection device provides a liquid transmission path communicating with exterior and sequentially passing through the first liquid transmission channel, the second liquid transmission channel, the third liquid transmission channel and the fourth liquid transmission channel; when the slide element is not pushed, the resilient valve returns to original state, such that the liquid transmission path is unable to communicate with the exterior.

2. The needle-free connection device according to claim 1, wherein the resilient valve comprises a deformable portion connected to the second hollow tube, and an isolation space is formed between the deformable portion and the second hollow tube and separates the first liquid transmission channel from the second liquid transmission channel.

3. The needle-free connection device according to claim 1, wherein the resilient valve further comprises a receiving portion, the second hollow tube extends from a lower surface of the receiving portion, the needle-free connection device further comprises a plurality of connection portions separated from each other and connecting the plug and an upper surface of the receiving portion, and a plurality of third liquid transmission channels separated from each other are formed between the connection portions.

4. The needle-free connection device according to claim 1, wherein the resilient valve further comprises a receiving portion, a deformable portion and a fourth hollow tube, the deformable portion and the fourth hollow tube respectively extend from two opposite sides of the receiving portion, and the fourth hollow tube extends linearly.

5. The needle-free connection device according to claim 1, wherein the resilient valve further comprises a fourth hollow tube disposed between the third hollow tube and the slide element, and the needle-free connection device further comprises a first sealing ring compressed between the third hollow tube and the fourth hollow tube.

6. The needle-free connection device according to claim 1, further comprising a second sealing ring compressed between the first hollow tube and the second hollow tube.

7. The needle-free connection device according to claim 1, wherein the resilient valve further comprises a receiving portion and a deformable portion, the deformable portion extends to an inner surface of the casing form a lower surface of the receiving portion, and a lower surface of the slide element and an upper surface of the receiving portion are disposed oppositely.

8. The needle-free connection device according to claim 1, wherein the casing comprises an engaging flange disposed on an inner sidewall of the casing, the connection base has a first engaging hole, and the engaging flange presses a bottom surface of the first engaging hole.

9. The needle-free connection device according to claim 1, wherein the slide element is protruded from a terminal surface of the connection base.

\* \* \* \* \*